(12) United States Patent
Riondel et al.

(10) Patent No.: US 6,875,889 B2
(45) Date of Patent: Apr. 5, 2005

(54) MONOMERS WITH QUATERNARY AMINO GROUPS, METHODS FOR MAKING SAME, AND NOVEL (CO)POLYMERS OBTAINED FROM SAID NOVEL MONOMERS

(75) Inventors: Alain Riondel, Forbach (FR); Vladimir Chaplinski, Saint Avoid (FR); Denis Tembou N'Zudie, Serquigny (FR)

(73) Assignee: ARKEMA, Puteaux (FR)

( * ) Notice: Subject to any disclaimer, the term of this patent is extended or adjusted under 35 U.S.C. 154(b) by 349 days.

(21) Appl. No.: 09/959,623

(22) PCT Filed: Jan. 19, 2001

(86) PCT No.: PCT/FR01/00180

§ 371 (c)(1),
(2), (4) Date: Oct. 18, 2002

(87) PCT Pub. No.: WO01/55088

PCT Pub. Date: Aug. 2, 2001

(65) Prior Publication Data

US 2003/0100679 A1 May 29, 2003

(30) Foreign Application Priority Data

Jan. 24, 2000 (FR) ............................................. 00 00836

(51) Int. Cl.$^7$ .............................................. C07C 69/54
(52) U.S. Cl. ....................... 560/222; 560/129; 560/205; 564/282; 564/291; 526/287; 526/292.2; 526/312; 526/328.5
(58) Field of Search ............................... 560/129, 205, 560/222; 564/282, 291; 526/287, 292.2, 312, 328.5

(56) References Cited

U.S. PATENT DOCUMENTS 3,586,711 A * 6/1971 Korshunov et al. .......... 560/222
6,469,204 B2 * 10/2002 Riondel et al. .............. 560/222
6,670,508 B2 * 12/2003 Riondel ....................... 564/282

OTHER PUBLICATIONS

Abstract of V.N. Ushakova et al.: "Radiation–induced copolymerization of N–Vinylpyrrolidone with quaternary ammonium salts of 1,3–bis(dimethylamino)isopropyl methacrylate" Russian Journal of Applied Chemistry., vol. 69, no. 2, 1996, pp. 270–273, XP002150046, Consultants Bureau., US, ISSN: 1070–4272, p. 271; table 1.
Solovskii, M. V. et al: "Synthesis and antimicrobial properties of mono– and polymeric quaternary ammonium salts containing aminoalkyl esters of methacrylic acid" KHIM.–FARM.ZH (1974), 8(6), 20–4, 1974, XP000952593, p. 348; table 1, p. 349.

Korshunov, M. A. et al: "Esters of .alpha.,.beta.–unsaturated acids with functional groups in the alkoxy radical. VII. Acrylates and methacrylates of monohydric polyamino alcohols" ZH. ORG. KHIM. (1969), 5(11), 1947–52, 1969, XP000952682, p. 1895; examples XX–XXIII.

* cited by examiner

Primary Examiner—Helen L. Pezzuto
(74) Attorney, Agent, or Firm—Millen, White, Zelano & Branigan, P.C.

(57) ABSTRACT

The invention relates to compounds of formula (I), prepared by quaternising a compound (II) by means of at least one compound $R^3\text{—}X^\ominus$:

$$\text{(I)}$$

$$\text{(II)}$$

$R^1$=H or —$CH_3$; $R^2$=—$CH_3$; —$C_2H_5$; —$C_3H_7$ or —$C_4H_9$; and compound (I) is optionally quaternised on one of the nitrogens, which is symbolised by the fact that the $R^3$, $X^\ominus$ and $\oplus$ associated with this nitrogen are shown between brackets; if compound (I) is quaternised on a single nitrogen, $R^3$ and $X^\ominus$ have the following meanings: (1) $R^3$=—$CH_3$ or —$CH_2C_6H_5$; and $X^\ominus$=$Cl^\ominus$ or $CH_3OSO_3^\ominus$; or (2) $R^3$=a $C_1$–$C_{12}$-alkyl group; and $X^\ominus$=$Br^\ominus$ or $I^\ominus$; if compound (I) is quaternised on both nitrogens, the two $X^\ominus$ may be the same or different and the two $R^3$ may be the same, in which case: (3) $R^3$=a $C_5$–$C_{12}$ alkyl group; and $X^\ominus$=$CH_3OSO_3^\ominus$, $Br^\ominus$ or $I^\ominus$; or different, in which case: (4) one of the $R^3$=—$CH_3$ or —$CH_2C_6H_5$; and $X^\ominus$=$Cl^\ominus$ or $CH_3OSO_3^\ominus$; and the other=a $C_5$–$C_{12}$-alkyl group; and $X^\ominus$=$Br^\ominus$ or $I^\ominus$.

15 Claims, No Drawings

MONOMERS WITH QUATERNARY AMINO GROUPS, METHODS FOR MAKING SAME, AND NOVEL (CO)POLYMERS OBTAINED FROM SAID NOVEL MONOMERS

The present invention relates to new monomers with quaternary amino groups, to a method of manufacturing same and to the new (co)polymers obtained from these new monomers.

Compounds of the type having formula:

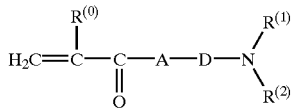

in which:

$R^{(0)}$ represents H or $CH_3$;

A represents —O— or —NH—;

D represents a $C_1$–$C_6$ linear or branched alkylene chain;

$R^{(1)}$ and $R^{(2)}$, the same or different, each represent independently H or $C_1$–$C_5$ alkyl;

are well known from the background literature.

Important compounds in this family are N,N-dimethylamino ethyl acrylate (ADAME) and N,N-dimethylamino ethyl methacrylate (MADAME):

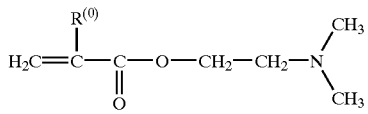

where $R^{(0)}$=H or $CH_3$.

A very large number of publications and patents describe the manufacture of aqueous solutions of quaternary ammonium salts based on ADAME and MADAME, the most representative of these salts being expressed by the formula:

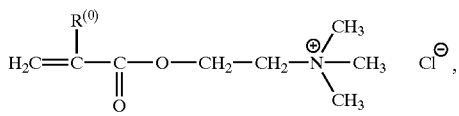

where $R^{(0)}$=H Or $CH_3$ and $R^{(3)}$=$CH_3$ or benzyl, these salts being designated by the abbreviation (M)ADAMQUAT MC or (M)ADAMQUAT BZ depending on whether $R^{(3)}$ represents $CH_3$ or benzyl.

This reaction is a quaternisation, in the presence of water, of the initial compound with a quaternising agent $R^{(3)}$—Cl.

The resultant aqueous solutions of quaternary salts are used in particular to prepare polymers intended for use as cationic flocculants in the treatment of water.

Patent CZ-A-250 962 discloses compounds of formula:

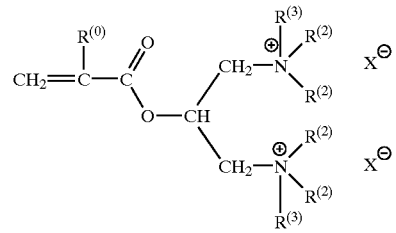

in which:

$R^{(0)}$ represents H or —$CH_3$;

$R^{(2)}$ represents —$CH_3$, —$C_2H_5$, —$C_3H_7$ or —$C_4H_9$;

$R^{(3)}$ represents —$CH_3$, —$C_2H_5$, —$C_3H_7$, —$C_4H_9$, $C_6H_5$ or —$CH_2C_6H_5$, and $X^{\ominus}$ represents $Cl^{\ominus}$ or $Br^{\ominus}$.

During research and development work, the applicant company has discovered new monomers which form the subject matter of the present application, together with a method of manufacturing same and the homo- or copolymers containing units derived from these new monomers.

Aqueous dispersions, either saline or without salt, made from these new monomers and offering a solution to technical problems faced by the person skilled in the art, are the subject matter of three French patent applications filed this day in the name of the applicant company.

Accordingly, the present invention relates firstly to compounds of formula (I):

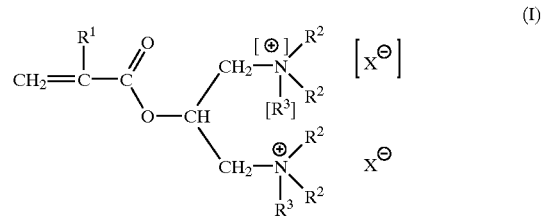

(I)

in which:

$R^1$ represents H or —$CH_3$;

$R^2$ represents —$CH_3$; —$C_2H_5$; —$C_3H_7$ or —$C_4H_9$; and compound (I) is optionally quaternised on one of the nitrogens, which is symbolised by the fact that the $R^3$, $X^{\ominus}$ and $\oplus$ associated with this nitrogen are shown between brackets;

if compound (I) is quaternised on a single nitrogen, $R^3$ and $X^{\ominus}$ have the following meanings:

(1) $R^3$ represents —$CH_3$ or —$CH_2C_6H_5$; and $X^{\ominus}$ represents $Cl^{\ominus}$ or $CH_3OSO_3^{\ominus}$; or (2) $R^3$ represents a $C_1$–$C_{12}$-alkyl group; and $X^{\ominus}$ represents $Br^{\ominus}$ or $I^{\ominus}$;

if compound (I) is quaternised on both nitrogens, the two $X^{\ominus}$ may be the same or different and the two $R^3$ may be the same, in which case:

(3) $R^3$ represents a $C_5$–$C_{12}$-alkyl group; and $X^{\ominus}$ represents $CH_3OSO_3^{\ominus}$, $Br^{\ominus}$ or $I^{\ominus}$;

or different, in which case:

(4) one of the $R^3$ represents —$CH_3$ or —$CH_2C_6H_5$; and $X^{\ominus}$ represents $Cl^{\ominus}$ or $CH_3OSO_3^{\ominus}$; and the other represents a $C_5$–$C_{12}$-alkyl group; and $X^{\ominus}$ represents $Br^{\ominus}$ or $I^{\ominus}$;

and mixtures of these compounds.

An example of a compound (I) is a compound having formula (Ia):

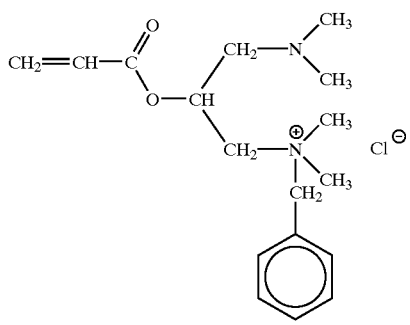

(Ia)

which may be designated by the abbreviation S-ADAMQUAT BZ.

The compounds proposed by the invention may advantageously be in aqueous solution.

The present invention also relates to a method of manufacturing compounds of formula (I) as defined above, characterised in that into a solution in an organic solvent or a mixture of organic solvents, of a compound of formula (II):

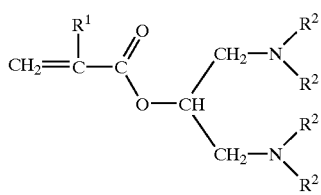

(II)

in which $R^1$ and $R^2$ are as defined above, is introduced, at a temperature of 35 to 80° C., a quaternising agent of formula (III):

$$R^3—X^\ominus \qquad (III)$$

in which:
  $R^3$ and $X^\ominus$ have the meanings (1) and (2) given above, in which case the molar ratio of quaternising agent (III)/compound (II) is in a range of between 0.9 and 1.5 and a compound (I) is obtained which is quaternised on a single nitrogen; or,
  $R^3$ and $X^\ominus$ have meaning (3) given above or two different quaternising agents are used, the $R^3$ and $X^\ominus$ of these two quaternising agents having meaning (4) given above, in which case the molar ratio of quaternising agent(s) (III)/compound (II) is in a range of between 0.9 and 1.5 and a compound (I) is obtained which is quaternised on both nitrogens,
then the reaction is allowed to continue at said temperature until compound(s) (III) has/have disappeared completely or substantially completely, after which water is added and then an aqueous solution of compound (I) is separated and the water removed as necessary.

The organic solvent(s) used is/are chloroform, dichloromethane, dichloroethane and mixtures thereof, for example.

The reaction is not generally conducted under pressure unless at least one quaternising agent (III) is in the gaseous state.

The quaternising agent(s) (III) is/are introduced into the solution of compound (II), generally over a period of 0.5 to 2 hours, and, once all the quaternising agent(s) has/have been introduced, the reaction of compounds (II) and (III) is conducted, generally over a period of 10 to 40 hours.

After separating the aqueous solution of compound (I), it is preferable to remove all traces of organic solvent from the resultant aqueous solution by stripping in air at a reduced pressure.

Said method results in an aqueous solution with a concentration of compound (I) which is preferably between 65 and 75% by weight.

According to one specific feature of the above method, it is conducted in the presence of at least one stabiliser selected in particular from hydroquinone, hydroquinone methyl ether and 3,5-ditert.-butyl-4-hydroxytoluene and mixtures of these stabilisers, the content of stabilising agent(s) being in particular 400 to 2000 ppm relative to the aqueous solution of the final compound (I).

Compound (II) may be prepared by causing a compound of formula (IV):

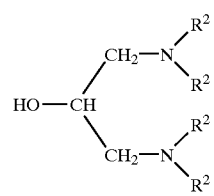

(IV)

in which $R^2$ is as defined above, to react with (meth)acrylic anhydride in the presence of triethylamine, with a molar ratio of (meth)acrylic anhydride/compound (IV) of 0.5 to 2, at a temperature of 20 to 100° C., in particular 30 to 60° C., for a period of 2 to 10 hours, in the presence of at least one stabiliser such as phenothiazine, hydroquinone methyl ether, 3,5-ditert.-butyl-4-hydroxytoluene and hydroquinone and mixtures of these stabilisers in a ratio of 200 to 3000 ppm relative to the charge.

In the reaction with (meth)acrylic anhydride, the triethylamine acts as a catalyst for the reaction and traps the (meth)acrylic acid in the salt form. It is generally used in an equivalent molar ratio of 1 to 2 relative to the (meth)acrylic anhydride.

Another objective of the present invention is to propose homopolymers or copolymers containing units of at least one monomer of formula (I) as defined above.

The copolymers based on the monomers (I) incorporating the monomer (Ia) may be water-soluble or hydrophobic polymers in the form of an aqueous dispersion, latex, aqueous solution, inverse, emulsion or powder. They are prepared by radical copolymerisation using various synthesis methods such as polymerisation in dispersion, solution, direct emulsion, inverse emulsion and inverse suspension.

The examples below, given by way of illustration only, provide a clearer understanding of the invention. In these examples, the specified proportions and percentages are by weight unless stated to the contrary.

The following abbreviations are used in these examples:
S-ADAME: compound of formula:

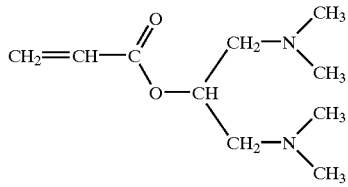

EMHQ: hydroquinone methyl ether.

EXAMPLE 1

Synthesis of S-ADAME

The following are introduced into a 1 liter glass reactor:
292 g of 1,3-bis-dimethylamino-2 propanol;
242 g of triethylaminre; and
0.373 g of phenothiazine as a stabiliser.

226 g of acrylic anhydride are then added to this mixture over a period of 1 hour at ambient temperature, under agitation and bubbling in air. The temperature increases, reaching 50° C. After an additional 2 hours reaction time, the mixture is cooled and 50 ml of water are added. After decanting, 450 g of a higher organic phase are obtained, which is distilled under reduced, pressure to separate 250 g of the above compound (purity GC≧99%).

EXAMPLE 2

Quaternisation of S-ADAME to Produce S-ADAMQUAT BZ

The S-ADAME obtained at point (a), stabilised with 1500 ppm of hydroquinone methyl ether and 150 g of $CHCl_3$, is introduced in a quantity of 44.2 g into a 250 ml glass reactor. Under agitation and whilst bubbling in air, the mixture is raised to 50° C. Over a period of 1 hour, 28 g of benzyl chloride are added. After a reaction time of 25 hours, the initial acrylate has disappeared and 33 g of water are added. A higher phase is decanted and any traces of $CHCl_3$ removed by air stripping at 45° C. under reduced pressure (P=1.33× $10^4$ Pa (100 mm Hg). 70 g of aqueous solution are thus obtained, containing 65% of quaternary cationic monomer of the anticipated structure, determined by RMN $^{13}C$. This-monomeris called S-ADAMQUAT BZ.

What is claimed is:
1. Compounds having formula (I):

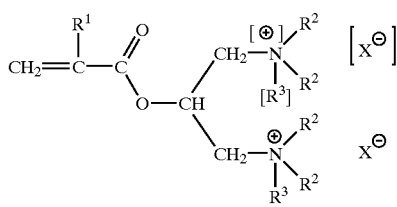

in which:
$R^1$ represents H or $-CH_3$;
$R^2$ represents $-CH_3$; $-C_2H_5$; $-C_3H_7$ or $-C_4H_9$; and
compound (I) is optionally quaternised on one of the nitrogens, which is symbolised by the fact that the $R^3$, $X^\ominus$ and $\oplus$ associated with this nitrogen are shown between brackets;

if compound (I) is quaternised on a single nitrogen, $R^3$ and $X^\ominus$ have the following meanings:
(1) $R^3$ represents $-CH_3$ or $-CH_2C_6H_5$; and $X^\ominus$ represents $Cl^\ominus$ or $CH_3OSO_3^\ominus$; or
(2) $R^3$ represents a $C_1-C_{12}$-alkyl group; and $X^\ominus$ represents $Br^\ominus$ or $I^\ominus$;

if compound (I) is quaternised on both nitrogens, the two $X^\ominus$ may be the same or different and the two $R^3$ may be the same, in which case:
(3) $R^3$ represents a $C_5-C_{12}$-alkyl; and $X^\ominus$ represents $CH_3OSO_3^\ominus$, $Br^\ominus$ or $I^\ominus$;
or different, in which case:
(4) one of the $R^3$ represents $-CH_3$ or $-CH_2C_6H_5$; and $X^\ominus$ represents $Cl^\ominus$ or $CH_3OSO_3^\ominus$; and
the other represents a $C_5-C_{12}$-alkyl group; and $X^\ominus$ represents $Br^\ominus$ or $I^\ominus$;
and mixtures of these compounds.

2. Compound as claimed in claim 1, characterised in that it is represented by the formula (Ia):

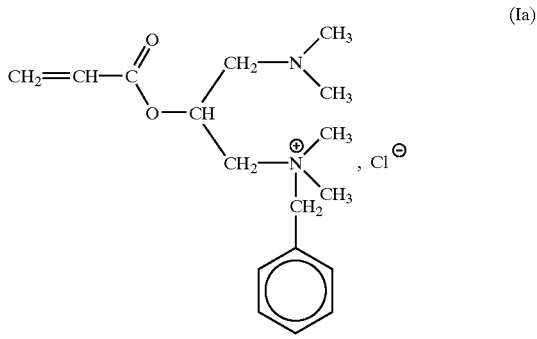

3. Compounds as claimed in one of claims 1 and 2, characterised in that they are in the form of an aqueous solution.

4. A method of manufacturing compounds as defined in claim 1, characterized in that into a solution in an organic solvent, of a compound of formula (II):

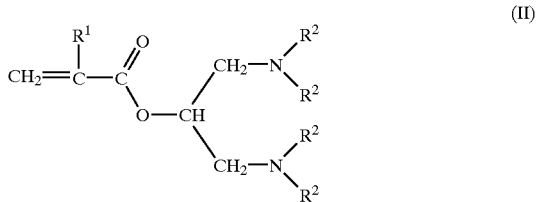

in which $R^1$ and $R^2$ are as defined in claim 1,
is introduced, at a temperature of 35 to 80° C., a quaternising agent of formula (III):

$$R^3-X^\ominus \qquad (III)$$

in which:
$R^3$ and $X^\ominus$ have the meanings (1) and (2) specified in claim 1, in which case the molar ratio of quaternising agent (III)/compound (II) is in a range of between 0.9 and 1.5 and a compound (I) is obtained which is quaternised on a single nitrogen; or
$R^3$ and $X^\ominus$ have meaning (3) specified in claim 1 or two different quaternising agents are used, the $R^3$ and $X^\ominus$ of these two quaternising agents having meaning (4) specified in claim 1, in which case the molar ratio of quaternising agent (s) (III)/compound (II) is in a range of between 0.9 and 1.5 and a compound (I) is obtained which is quaternised on both nitrogens,
then the reaction is allowed to continue at said temperature until compound(s) (III) has/have disappeared completely or substantially completely, after which water is added and then an aqueous solution of compound (I) is separated and the water removed as necessary.

5. A method as claimed in claim 4, characterised in that the organic solvent used is at least one selected from chloroform, dichloromethane and dichloroethane.

6. A method as claimed in claim 4, characterized in that it is conducted under pressure if the quaternising agent or at least one quaternising agent (III) is in the gaseous state.

7. A method as claimed in claim 4, characterized in that the quaternising agent or quaternising agents (III) is/are introduced into the solution of compound (II) over a period of 0.5–2 hours.

8. A method as claimed in claim 4, characterized in that once all of thee quaternising agent or quaternising agents has/have been introduced, the reaction between compounds (II) and (III) is conducted for a period of between 10 and 40 hours.

9. A method as claimed in claim 4, characterized in that all traces of organic solvent are removed from the resultant aqueous solution by stripping in air at a reduced pressure.

10. A method as claimed in claim 4, characterized in that it produces an aqueous solution with a concentration of 65 to 75% by weight of compound (I).

11. A method as claimed in claim 4, characterized in that it is conducted in the presence of at least one stabiliser chosen in particular from hydroquinone, hydroquinone methyl ether and 3,5-ditert.-butyl-4-hydroxytoluene and mixtures of these stabilisers, the content of stabilising agent (s) being in particular from 400 to 2000 ppm relative to the aqueous solution of the final compound (I).

12. A method as claimed in claim 4, characterized in that compound (II) is prepared by causing a compound of formula (IV):

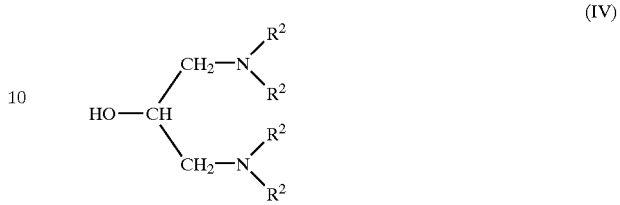

in which $R^2$ is as defined above,
to react with (meth)acrylic anhydride in the presence of triethylamine, with a molar ratio of (meth)acrylic anhydride/ compound (IV) of 0.5 to 2, at a temperature of 20 to 100° C., in particular 30 to 60° C., for a period of 2 to 10 hours in the presence of at least one stabiliser.

13. Homopolymers or copolymers containing units of at least one monomer of formula (I) as defined in claims 1 to 3.

14. Homopolymers or copolymers containing units of at least one monomer of formula (I) as defined in claim 2.

15. A method as claimed in claim 12, wherein said stabilizer is selected from the group consisting of phenothiazine, hydroquinone methyl ether, 3,5-ditert.-butyl-4-hydroxytoluene and hydroquinone and mixtures, of these stabilisers in a ratio of 200 to 3000 ppm relative to the charge.

* * * * *

UNITED STATES PATENT AND TRADEMARK OFFICE
CERTIFICATE OF CORRECTION

PATENT NO. : 6,875,889 B2
DATED : April 5, 2005
INVENTOR(S) : Riondel et al.

It is certified that error appears in the above-identified patent and that said Letters Patent is hereby corrected as shown below:

<u>Column 6,</u>
Line 35, reads "one of claims 1 and 2" should read -- claims 1 --.
Line 40, reads "solvent," should read -- solvent or a mixture of organic solvents --.

<u>Column 7,</u>
Line 19, reads "thee" should read -- the --.
Line 33, reads "agent" should read -- agent(s) --.

<u>Column 8,</u>
Line 23, reads "claims 1 to" should read -- claim 1. --.
Line 24, delete entire line.
Line 29, reads "mixtures," should read -- mixture --.

Signed and Sealed this

Nineteenth Day of July, 2005

JON W. DUDAS
*Director of the United States Patent and Trademark Office*